United States Patent
Choi

(10) Patent No.: US 11,685,952 B2
(45) Date of Patent: Jun. 27, 2023

(54) BIOMARKER FOR PREDICTING RISK OF RECURRENCE IN PATIENTS WITH PAROXYSMAL ATRIAL FIBRILLATION

(71) Applicant: KOREA UNIVERSITY RESEARCH AND BUSINESS FOUNDATION, Seoul (KR)

(72) Inventor: Jong Il Choi, Seoul (KR)

(73) Assignee: KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 54 days.

(21) Appl. No.: 16/928,828

(22) Filed: Jul. 14, 2020

(65) Prior Publication Data

US 2021/0207216 A1    Jul. 8, 2021

(30) Foreign Application Priority Data

Jan. 7, 2020 (KR) .................. 10-2020-0001844

(51) Int. Cl.
   *C12Q 1/68*  (2018.01)
   *C12P 19/34* (2006.01)
   *C12Q 1/6883* (2018.01)
   *C12Q 1/37* (2006.01)

(52) U.S. Cl.
   CPC ........... *C12Q 1/6883* (2013.01); *C12Q 1/37* (2013.01); *C12Q 2600/118* (2013.01); *C12Q 2600/156* (2013.01)

(58) Field of Classification Search
   CPC ........... C12Q 1/6883; C12Q 2600/118; C12Q 2600/156; G01N 2800/54
   See application file for complete search history.

(56) References Cited

U.S. PATENT DOCUMENTS

2011/0009861 A1    1/2011    Mukherjee et al.

FOREIGN PATENT DOCUMENTS

KR    1020190009341 A    1/2019

OTHER PUBLICATIONS

MR Luizon, et al. "Tissue inhibitor of matrix metalloproteinase-1 polymorphism, plasma TIMP-1 levels, and antihypertensive therapy responsiveness in hypertensive disorders of pregnancy", The Pharmacogenomics Journal (2014) 14, 535-541 (Year: 2014).*
Marlena Matulka et al., "Expression and Concentration of Matrix Metalloproteinase 9 and Tissue Inhibitor of Matrix Metalloproteinases 1 in Laryngeal Squamous Cell Carcinoma" Disease Markers, vol. 2019, Article ID 3136792, 9 pages (Year: 2019).*
Babar Parvez, et al, "Symptomatic Response to Antiarrhythmic Drug Therapy Is Modulated by a Common Single Nucleotide Polymorphism in Atrial Fibrillation" Journal of the American College of Cardiology, vol. 60, No. 6, 2012, pp. 539-545 (Year: 2012).*
Eleftherios M. Kallergis, et al., "Extracellular Matrix Alterations in Patients With Paroxysmal and Persistent Atrial Fibrillation" Journal of the American College of Cardiology, vol. 52, No. 3, 2008, pp. 211-215. (Year: 2008).*
Choi, Jong-Il et al. Chromosome 4q25 variants and biomarkers of myocardial fibrosis in patients with atrial fibrillation, Journal of Cardiovascular Electrophysiology, 2019; 30: 1904-1913.
Husser, D. et al. Chromosome 4q25 Variants and Atrial Fibrillation Recurrence After Catheter Ablation, Journal of the American College of Cardiology, vol. 55, No. 8, 2010, pp. 747-753.

* cited by examiner

*Primary Examiner* — Stephen T Kapushoc
(74) *Attorney, Agent, or Firm* — Casimir Jones, S.C.; Tanya A. Arenson

(57) ABSTRACT

A method of providing information for predicting a risk of a recurrence after treatment of a patient with paroxysmal atrial fibrillation (AF) is provided. The method includes measuring a concentration of tissue inhibitor of metalloproteinase (TIMP)-1 from a sample isolated from a patient, and detecting a presence of a genetic variant at rs10033464 GG on chromosome 4q25 from nucleic acid separated from the sample.

4 Claims, 6 Drawing Sheets

BIOMARKER FOR PREDICTING RISK OF RECURRENCE IN PATIENTS WITH PAROXYSMAL ATRIAL FIBRILLATION

CROSS-REFERENCE TO RELATED APPLICATION(S)

This application claims the priority benefit of Korean Patent Application No. 10-2020-0001844, filed on Jan. 7, 2020, in the Korean Intellectual Property Office, the disclosure of which is incorporated herein by reference for all purposes.

BACKGROUND

1. Field

One or more example embodiments relate to a biomarker for predicting a risk of a recurrence in a patient with paroxysmal atrial fibrillation (AF).

2. Description of Related Art

Cardiac arrhythmia is a disorder in which a heart rhythm is disturbed and is associated with serious diseases such as stroke or sudden death. Atrial fibrillation (AF) is the most common type of arrhythmia, and its prevalence is increasing worldwide due to aging. The AF is refractory arrhythmia with a high drug resistance and a recurrence rate of 10% to 30% even after surgery even though a good prognosis has been demonstrated when a normal pulse is maintained, and is accompanied by a risk of stroke of 6% to 10% per year. In Korea, patients with AF are more clearly increasing due to the recent progress of aging of the society. The prevalence of AF in Korea has increased by 2.1 times over the past 10 years, from 0.73% in 2006 to 1.53% in 2015, and is higher in men than in women.

According to the 2014 AHA/ACC/HRS guidelines, paroxysmal AF refers to AF that ends spontaneously or ends within seven days of intervention. Persistent AF refers to AF that lasts more than seven days, and long-standing AF refers to a case in which AF lasts more than one year. It was found that one of three patients with paroxysmal AF who temporarily experience AF progressed to persistent AF continued for at least seven days within ten years. Also, it was found that about half of patients with paroxysmal AF lead to persistent AF or death for ten years.

Recently, in small-scale studies that examine factors contributing to a recurrence of AF after electrical cardioversion, a large number of studies showing that stromal derived factor (SDF)-1a and transforming growth factor (TGF)-β are related have been conducted. In Europe, in a study that analyzed three major loci (PITX2, ZFHX3, and KCNN3) associated with AF and catheter ablation results in 991 patients, PITX2, ZFHX3, and KCNN3 were identified as major genes. In contrast, in a study of 1068 Koreans, experiments were conducted with PITX2, ZFHX3, and KCNN3 that are similar sets of single-nucleotide polymorphisms (SNPs), but there was no significant difference in a recurrence of AF in long-term follow-up after catheter resection.

PRIOR ART DOCUMENT

Patent Document (Patent Document 1) Korean Patent Application Publication No. 10-2019-0009341

SUMMARY

An aspect is to provide information for predicting a risk of a recurrence after treatment based on a blood concentration of tissue inhibitor of metalloproteinase (TIMP)-1 in patients with paroxysmal atrial fibrillation (AF) and a genetic variation of rs10033464.

However, problems to be solved by the present disclosure are not limited to the above-described problems, and other problems not mentioned herein can be clearly understood by those skilled in the art from the following descriptions.

According to an example embodiment, there is provided a method of predicting a risk of a recurrence after treatment of a patient with paroxysmal AF, the method including measuring a concentration of TIMP-1 from a sample isolated from a patient, and detecting a presence of a genetic variation at rs10033464 on chromosome 4q25 from nucleic acid separated from the sample.

When the concentration of the TIMP-1 is 107 ng/ml or greater, and when the genetic variation at the rs10033464 is present, the risk of the recurrence after the treatment may be determined to be high.

A genotype of the genetic variation at the rs10033464 may be GT or TT.

The treatment may be surgical treatment or pharmacological treatment.

The surgical treatment may be catheter ablation, cryoablation, or a surgical operation.

The sample may be whole blood, a serum, or plasma.

The detecting of the presence of the genetic variation at the rs10033464 may be performed by at least one method among a hybridization by a microarray, an allele-specific polymerase chain reaction (PCR), a dynamic allele-specific hybridization (DASH), a PCR extension assay, a PCR-single-strand conformation polymorphism (SSCP), a PCR-restriction fragment length polymorphism (RFLP), and a TaqMan scheme.

Additional aspects of example embodiments will be set forth in part in the description which follows and, in part, will be apparent from the description, or may be learned by practice of the disclosure.

According to example embodiments, a risk of a recurrence after treatment of a patient with AF, in particular, paroxysmal AF, may be predicted using the above-described method and thus the method may be usefully applied as an examination method before surgical or pharmacological treatment.

Also, a clinical condition of a patient may be analyzed in advance through a simple examination and patient-specific treatment may be conducted, and thus it is possible to reduce the risk of the recurrence and the burden of social cost for medical care.

It should be understood that the effects of the present disclosure are not limited to the aforementioned effects, and include all of the effects deducible from the detailed description of the present disclosure or the configuration of the invention described in the claims.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1A:
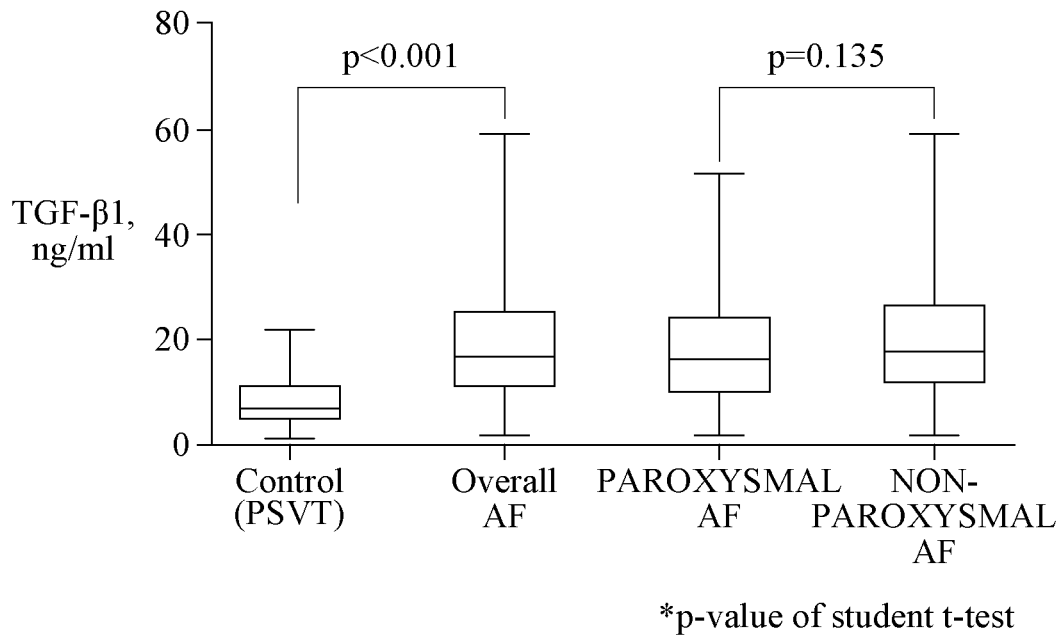
FIGS. 1A and 1B illustrate comparisons of plasma levels of transforming growth factor (TGF)-β1 and tissue inhibitor of metalloproteinase (TIMP)-1 among a control group (hereinafter, referred to as "control paroxysmal supraventricular tachycardia (PSVT)"), an overall AF group of patients with atrial fibrillation (AF), a paroxysmal AF group of patients with paroxysmal AF, and a non-paroxysmal AF group of patients with persistent AF.

Hereinafter, example embodiments will be described in detail with reference to the accompanying drawings. However, various alterations and modifications may be made to the example embodiments. Here, the example embodiments are not construed as limited to the disclosure and should be understood to include all changes, equivalents, and replacements within the idea and the technical scope of the disclosure.

The terminology used herein is for the purpose of describing particular example embodiments only and is not to be limiting of the example embodiments. As used herein, the singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the example embodiments with reference to the accompanying drawings, like reference numerals refer to like constituent elements and a repeated description related thereto will be omitted. In the description of the example embodiments, detailed description of well-known related structures or functions will be omitted when it is deemed that such description will cause ambiguous interpretation of the present disclosure.

Hereinafter, terms used herein will be briefly described.

The term "rs10033464" used herein is a single-nucleotide polymorphism (SNP) on chromosome 4q25, and refers to a SNP identified by number "rs10033464" in dbSNP database of the National Center for Biotechnology Information (NCBI) in USA.

The term "atrial fibrillation (AF)" used herein is a type of arrhythmia disease that causes irregular pulses by rapidly forming waveforms at a heart rate of 300 to 600 beats per minute during irregular beating of atrial chambers. The AF may be categorized according to its duration into "paroxysmal AF" that ends within one week of an occurrence, and "persistent AF" that lasts more than one week and that is referred to as "non-paroxysmal AF".

The term "catheter ablation" used herein refers to surgery of finding the cause of tachycardia through an electric physiologic test, placing an electrode catheter in a source region of the tachycardia, and removing the source region. The catheter ablation may be classified into radiofrequency catheter ablation and cryogenic catheter ablation, according to a removal method.

The term "recurrence" used herein is defined as recurrent AF, atrial flutter, or atrial tachycardia (AT) that lasts more than 30 seconds after the lapse of more than 3 months from catheter ablation in accordance with the 2012 HRS/EHRA/ECAS expert consensus statement.

According to an example embodiment, a method of predicting a risk of a recurrence after treatment of a patient with paroxysmal AF may be provided. The method may include measuring a concentration of tissue inhibitor of metalloproteinase (TIMP)-1 from a sample isolated from a patient, and detecting a presence of a genetic variation at rs10033464 on chromosome 4q25 from nucleic acid separated from the sample.

When the concentration of the TIMP-1 is 107 ng/ml or greater, and when the genetic variation at the rs10033464 is present, the risk of the recurrence after the treatment may be determined to be high. Specifically, a genotype of the genetic variation at the rs10033464 may be GT or TT.

The treatment may include surgical treatment or pharmacological treatment, and accordingly the TIMP-1 and rs10033464 may be used in companion diagnostics before treatment of a patient with AF.

The surgical treatment may include, but is not limited to, for example, a medical procedure such as catheter ablation or cryoablation, and a surgical operation such as thoracoscopic arrhythmia surgery. For example, the surgical treatment may include all possible surgeries or procedures.

The pharmacological treatment may include, but is not limited to, for example, an antiarrhythmic agent such as propaphenone, flecainide, pilsicainide, amiodarone, sotalol or dronedarone, a heart rate control agent such as digoxin, beta blockers, verapamil or diltiazem, an anticoagulant agent, and an antiplatelet agent.

The sample to which the method is applicable may be whole blood, a serum, or plasma, but is not limited thereto.

In the method, the detecting of the presence of the genetic variation at the rs10033464 may be performed by at least one method among a hybridization by a microarray, an allele-specific polymerase chain reaction (PCR), a dynamic allele-specific hybridization (DASH), a PCR extension assay, a PCR-single-strand conformation polymorphism (SSCP), a PCR-restriction fragment length polymorphism (RFLP), and a TaqMan scheme, but is not limited thereto.

Hereinafter, example embodiments will be described in more detail with reference to examples.

1. Study Design

Patients (158 patients with paroxysmal AF and 137 patients with non-paroxysmal AF) who underwent catheter ablation of AF between Mar. 25, 2009 and Oct. 15, 2012 at Korea University Hospital in Seoul, South Korea, or patients with paroxysmal supraventricular tachycardia (PSVT) who have no AF and underwent catheter ablation between Jun. 27, 2011 and Sep. 7, 2012 at Korea University Hospital were included in the present study. The patients with PSVT who underwent the catheter ablation served as a control group, because they had neither clinical evidence of AF based on 24 to 48 hours Holter monitoring or electrocardiography (ECG) nor prior history of AF.

The design of the present study was approved by the Institutional Review Board at Korea University Hospital, and all patients were provided informed consent.

2. Subject Selection

As patients with symptomatic/drug-resistant paroxysmal and persistent AF, patients aged 19 years or older who underwent catheter ablation were included. Patients with supraventricular tachycardia (SVT), aged 40 years or less, who underwent catheter ablation and have no history of atrial flutter were included in the control group.

The following patients were excluded: repeat/redo catheter ablation, myocardial infarction or unstable angina in the previous two months, rheumatic heart disease, congenital heart disease or atrial septal defects, hypertrophic cardiomyopathy, left ventricular ejection fraction less than 35%, New York Heart Association (NYHA) class IV heart failure, stroke, or transient ischemic attack in the past month; women who are known to be pregnant or have had a positive (β-human chorionic gonadotropin (HCG) test seven days prior to a procedure, women who have coagulopathy, life expectancy less than one year, prior sustained ventricular arrhythmia, corrected QT interval of less than 500 msec, or mental disorders that prevent patients from providing informed consent or performing an appropriate follow-up.

3. Biomarker Measurements

Blood samples were obtained after a femoral vein access but before a transseptal access and ablation. The obtained blood samples were centrifuged and stored at −80° C. and were used in a laboratory. Concentrations of TIMP-1 and TGF-β1 were measured using commercially available kits (Quantikine Human ELISA Kit) and genotyping for SNPs on chromosome 4q25 were performed by a TaqMan method.

4. Statistical Analysis

Continuous variables were reported as mean±standard deviation or medians and interquartile ranges, and categorical variables were expressed as percentages and frequencies. Comparisons between the above two groups were performed using an independent sample t-test or chi-square test. Analysis of variance (ANOVA) was used to verify whether three groups differ with respect to continuous parameters. An area under curve (AUC) and cutoff points for fibrosis biomarkers were identified by receiver operating characteristic (ROC) curves. Freedom from AF recurrence was estimated using Kaplan-Meier methods by a logrank test, and Cox proportional hazard modeling was adjusted for factors associated with AF recurrence selected through a regression analysis with a retention criterion a of 0.05. Relevance adjusted for the freedom from AF recurrence using Bonferroni correction was reported as a hazard ratio (HR) and 95% confidence intervals (CI). Two-sided P values of 0.05 or less were considered statistically significant. Data analyses were performed using SPSS Statistics 17.0 software (SPSS Inc., Armonk, N.Y., USA).

Example 1. Result of Comparison in Blood Concentrations of TIMP-1 and TGF-β1

Figure 1B:
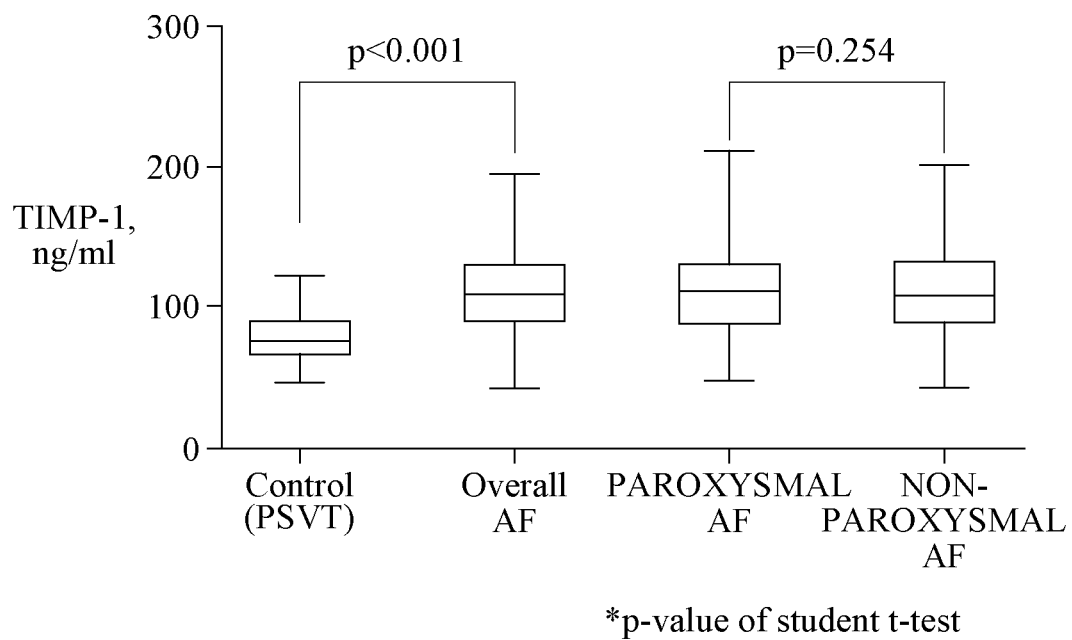

As results of comparisons of concentrations of TIMP-1 and TGF-β1 among the control (PSVT) and AF patient group from the obtained blood samples, it is confirmed that plasma levels of TIMP-1 and TGF-β1 were relatively high in patients with AF in comparison to the control (PSVT), as shown in FIGS. 1A and 1B (8.4±5.6 vs. 18.7±10.5 ng/ml, p<0.001; 77.3±16.5 vs. 113.5±43.7 ng/ml, p<0.001).

Comparing patients with paroxysmal AF and patients with persistent AF, there was no statistically significant difference in the plasma levels of TIMP-1 and TGF-β1 (17.8±9.9 vs. 19.6±11.0 ng/ml, p=0.135; 110.8±33.7 vs. 116.7±52.8 ng/ml, p=0.254).

Example 2. Comparison of Chromosome 4q25 Genotypes

The cohort was genotyped at a call rate of 98.6% for both SNPs, that is, rs10033464 and rs2200733. Hardy-Weinberg equilibrium of genotype distribution of polymorphisms was preserved in the control group and the patients with AF.

TABLE 1

|  | Control (PSVT) | Overall AF | | Overall AF | | |
| --- | --- | --- | --- | --- | --- | --- |
|  | (n = 70) | (n = 295) | p-value | Paroxysmal | Non-paroxysmal | p-value |
| rs10033464 |  |  | 0.152 |  |  | 0.503 |
| GG, n (%) | 40 (57.1) | 209 (70.8) |  | 109 (69.0) | 100 (73.0) |  |
| GT, n (%) | 27 (38.6) | 74 (25.1) |  | 43 (27.2) | 31 (22.6) |  |
| TT, n (%) | 2 (2.9) | 8 (2.7) |  | 5 (3.2) | 3 (2.2) |  |
| Failed genotyping, n (%) | 1 (1.4) | 4 (1.4) |  | 1 (0.6) | 3 (2.2) |  |
| rs2200733 |  |  | <0.001 |  |  | 0.599 |
| CC, n (%) | 16 (22.9) | 32 (10.8) |  | 19 (12.0) | 13 (9.5) |  |
| CT, n (%) | 38 (54.3) | 111 (37.6) |  | 63 (39.9) | 48 (35.0) |  |
| TT, n (%) | 16 (22.9) | 147 (49.8) |  | 73 (46.2) | 74 (54.0) |  |
| Failed genotyping, n (%) | 0 (0) | 5 (1.7) |  | 3 (1.9) | 2 (1.5) |  |

Results obtained by investigating frequencies of rs10033464 and rs2200733 showed that a relatively high frequency of a risk allele carrier at rs2200733 is present in the patients with AF in comparison to the control group and that frequencies are similar at rs10033464 (CC: 22.9% vs. 10.8%; CT: 54.3% vs. 37.6%; TT: 22.9% vs. 49.8%), as shown in Table 1. However, there was no great difference in the genotype distribution at rs10033464 and rs2200733 between patients with paroxysmal AF and patients with persistent AF.

Example 3. Response to Catheter Ablation of Patients with AF

Over a mean follow-up assessment period of 3.1±1.1 years, 40 of 158 patients with paroxysmal AF (25.3%) and 76 of 137 patients with persistent AF (55.5%) experienced a recurrence of AF and/or AT. One-year follow-up recurrence rates were 17.7% in patients with paroxysmal AF and 40.9% in patients with persistent AF. A mean plasma level of TIMP-1 was relatively high in patients with recurrent AT/AF in comparison to patients without recurrent AT/AF (120.0±53.1 vs. 109.3±35.8 ng/mL, p=0.039), and there was no statistically significant difference in the level of TGF-β1 (19.6±9.7 vs. 18.0±10.9 ng/mL; p=0.201).

Figure 2A:
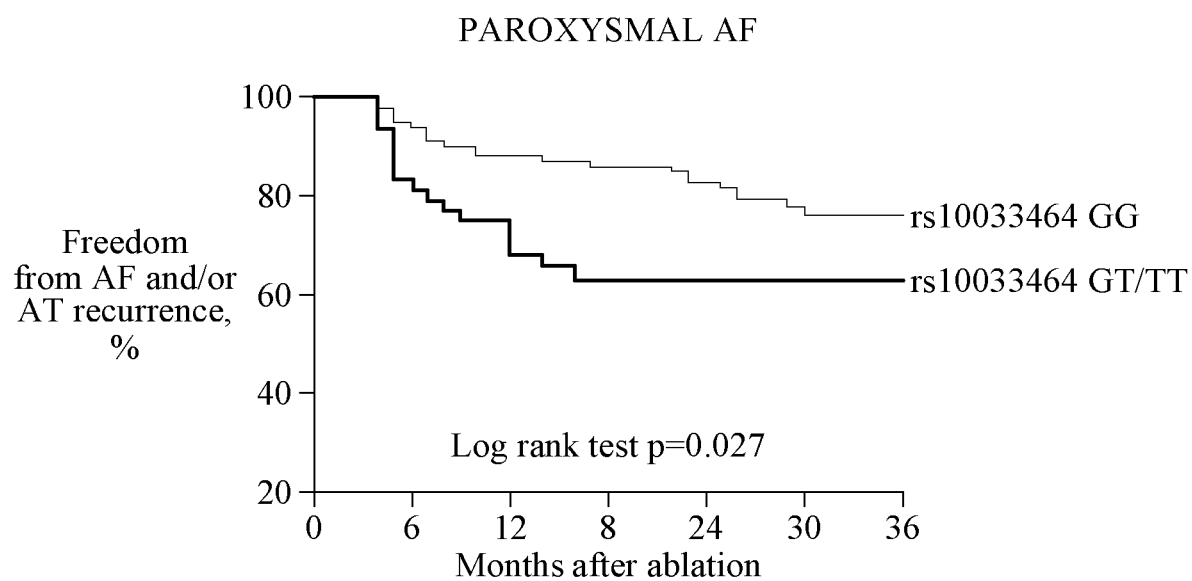
FIGS. 2A and 2B illustrate comparisons of freedom from recurrence of AF after catheter ablation based on genotypes of rs10033464 of patients with paroxysmal AF and patients with persistent AF through Kaplan-Meier analyses.
Figure 2B:
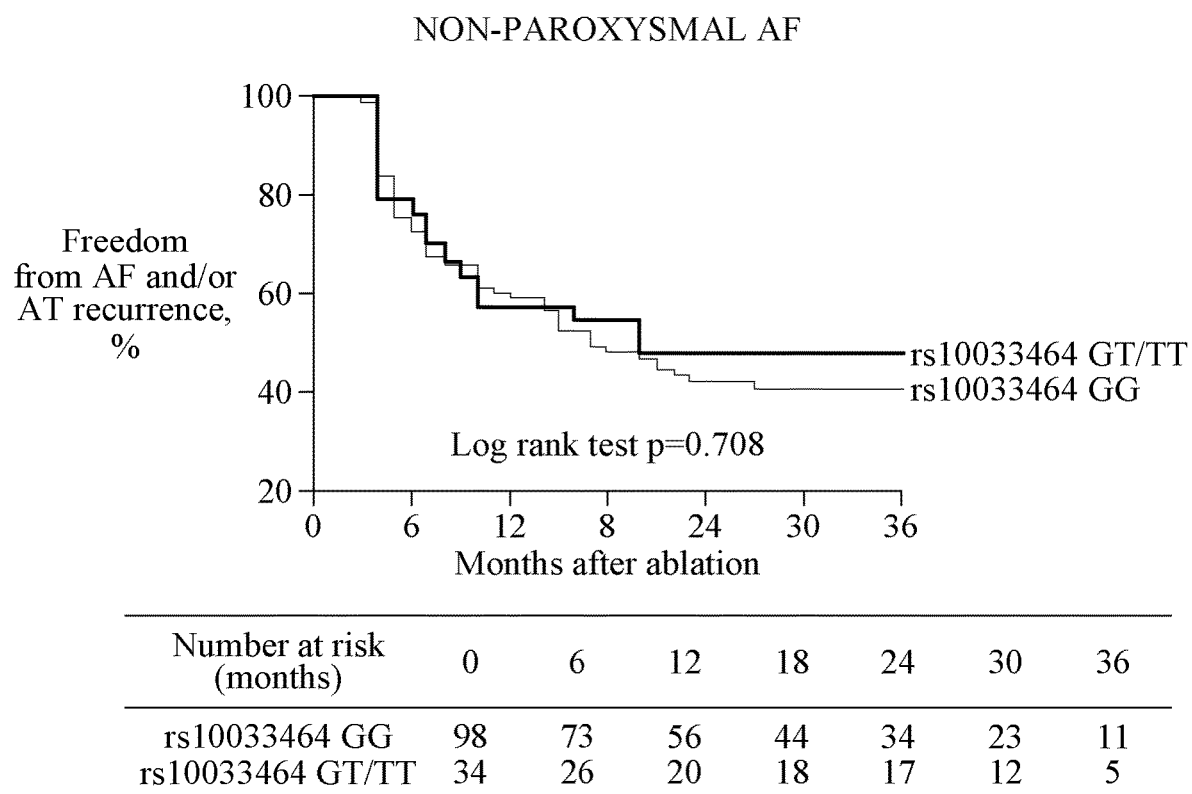

Optimal cut-off values of TGF-β1 and TIMP-1 for recurrence, determined by a ROC curve, were 17 ng/ml (AUC=0.558) and 107 ng/ml (AUC=0.567), respectively. In comparison to patients in the control group, patients with variant alleles of rs1003346 were observed to have increased recurrence after the patients with paroxysmal AF underwent the catheter ablation (p=0.027, by logrank test), however, the result was similar in patients with persistent AF (p=0.708; FIGS. 2A and 2B).

Example 4. Relationship Between Recurrence Rate after Catheter Ablation and Combination of Variant Alleles of Rs1003346 and Blood Concentration of TIMP-1

Figure 3A:
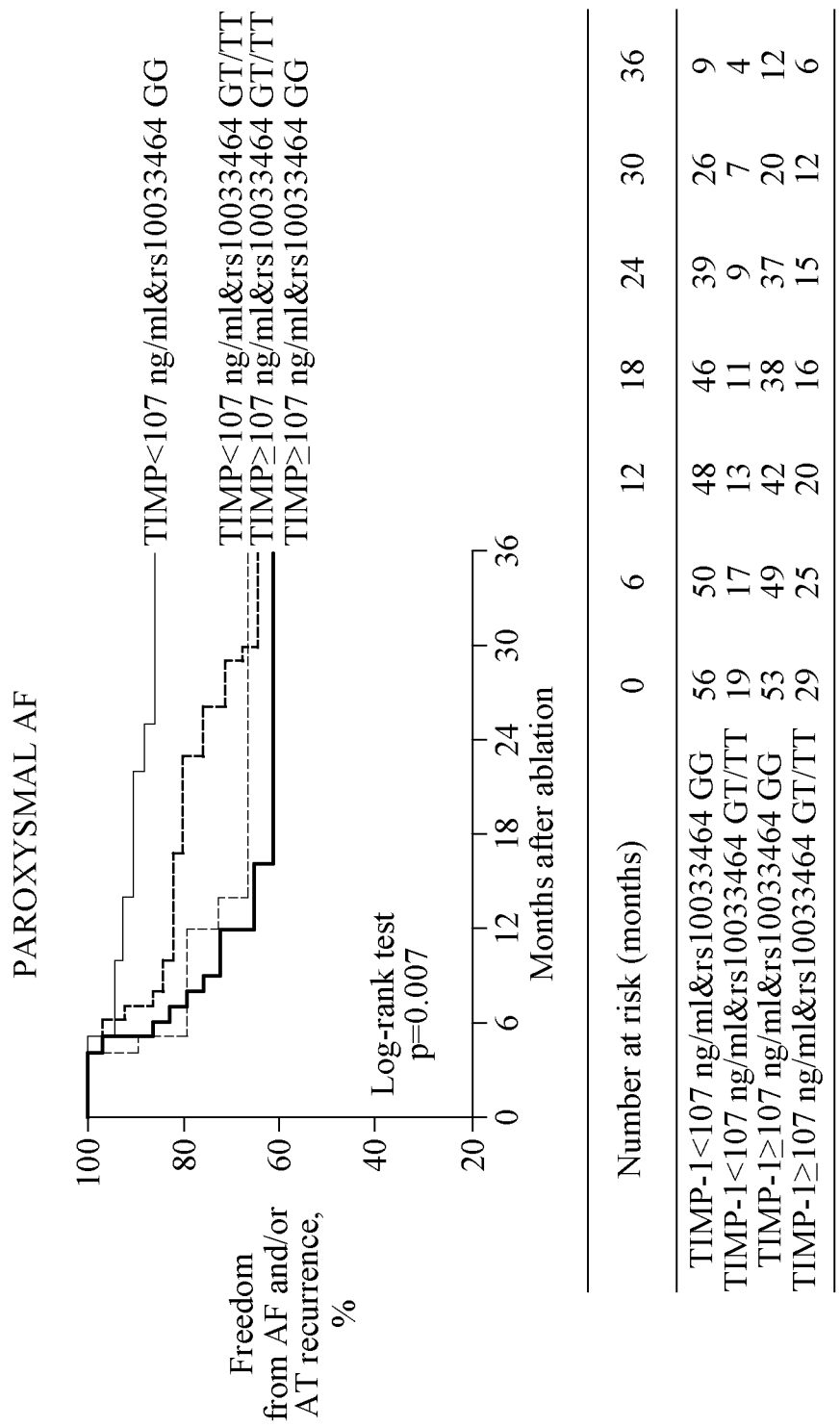
FIGS. 3A and 3B illustrate comparisons of freedom from recurrence of AF after catheter ablation when plasma levels of TIMP-1 and genotypes of rs10033464 of patients with paroxysmal AF and patients with persistent AF are combined, through Kaplan-Meier analyses.
Figure 3B:
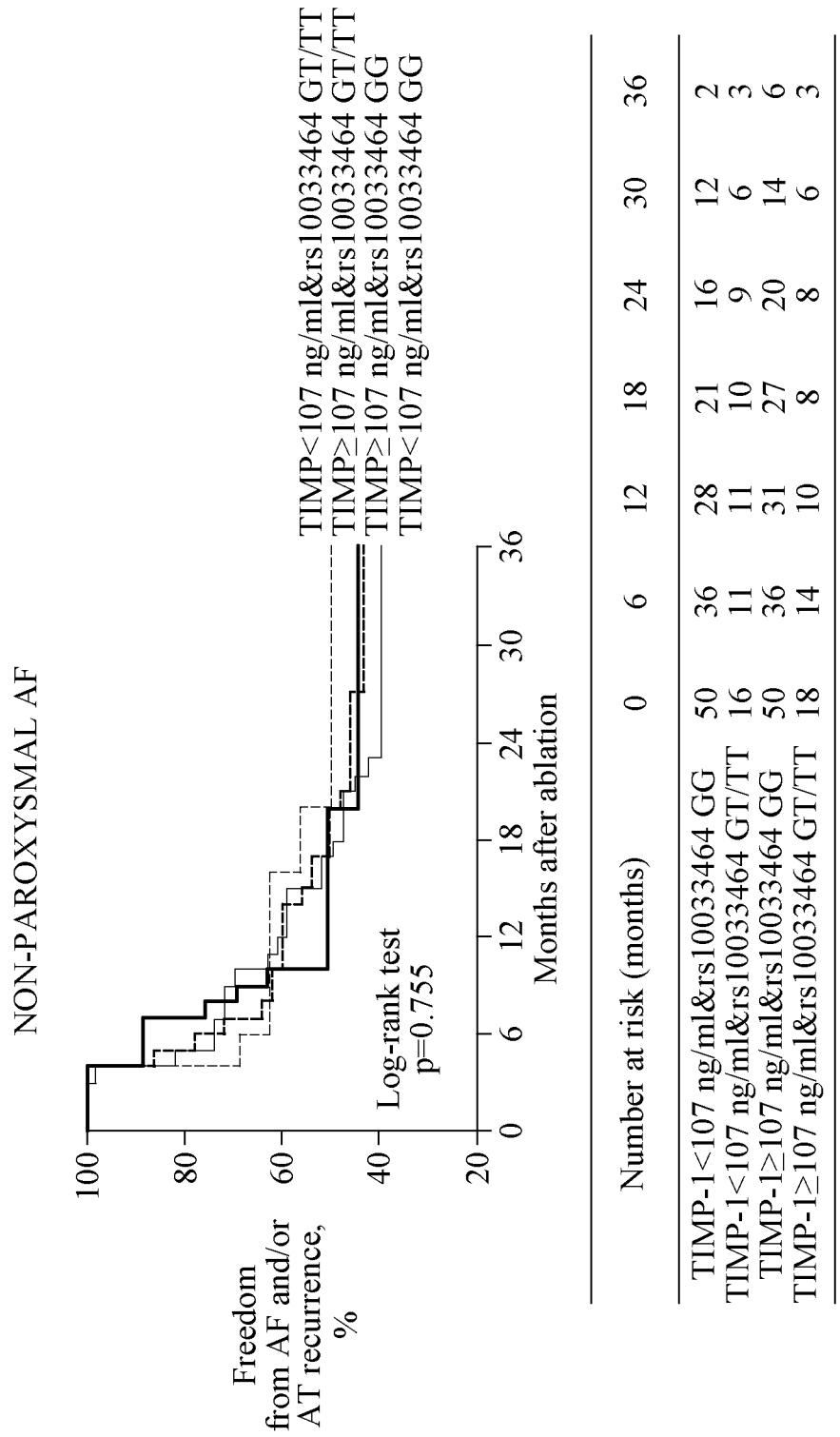

When the blood concentration of TIMP-1 and risk allele of rs10033464 are combined and used, TIMP-1 is less than 107 ng/ml in patients with paroxysmal AF, and patients without a variant allele (GG) at rs10033464 have a relatively low recurrence rate in comparison to a group of patients with TIMP-1 of 107 ng/ml or greater, or a group of patients with variant alleles GT and TT (logrank, p=0.007), as shown in FIG. 3A. Also, when added to CHA$_2$DS$_2$-VASc scores, the concentration of TIMP-1 and genotype improved C-statistics for an AF recurrence after catheter ablation in patients with paroxysmal AF, but not in patients with persistent AF, as shown in Table 2. In other words, there was no statistically significant difference in the patients with persistent AF.

TABLE 2

|  | C-statistics (95% CI) | p-value | p-value for comparison of C-statistics with CHA$_2$DS$_2$-VASc scores |
|---|---|---|---|
| Paroxysmal AF | | | |
| CHA$_2$DS$_2$-VASc score | 0.499 (0.418-0.579) | 0.978 | |
| CHA2DS2-VASc score + LA diameter | 0.519 (0.439-0.599) | 0.673 | 0.996 |
| CHA2DS2-VASc score + TIMP-1 | 0.567 (0.486-0.645) | 0.154 | 0.468 |
| CHA2DS2-VASc score + genotype | 0.550 (0.469-0.629) | 0.285 | 0.432 |
| CHA2DS2-VASc score + TIMP-1 + genotype | 0.600 (0.519-0.677) | 0.038 | 0.047 |
| Non-paroxysmal AF | | | |
| CHA$_2$DS$_2$-VASc score | 0.523 (0.436-0.609) | 0.564 | |
| CHA2DS2-VASc score + LA diameter | 0.499 (0.413-0.586) | 0.985 | 0.351 |
| CHA2DS2-VASc score + TIMP-1 | 0.502 (0.415-0.588) | 0.969 | 0.529 |
| CHA2DS2-VASc score + genotype | 0.512 (0.425-0.598) | 0.797 | 0.608 |
| CHA2DS2-VASc score + TIMP-1 + genotype | 0.495 (0.408-0.581) | 0.912 | 0.461 |

Figure 4:
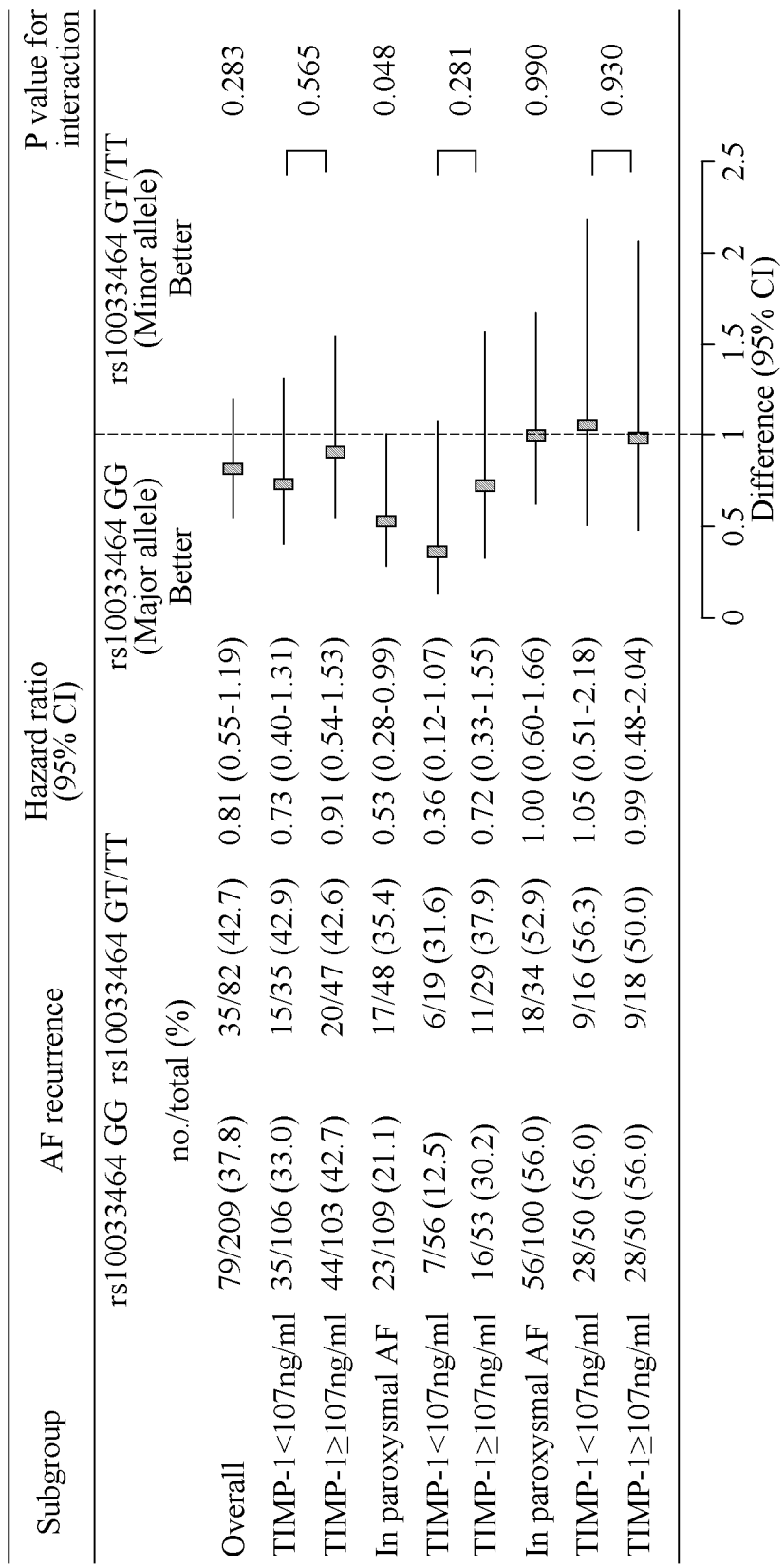
FIG. 4 illustrates a hazard ratio (HR) for an influence of a genotype of rs10033464 on a recurrence of AF in subgroups of patients with AF based on a concentration of TIMP-1.

Subsequently, the HR (95% CI) for an influence of rs10033464 on a recurrence of AF based on 107 ng/ml that is the blood concentration of TIMP-1 was confirmed. As a result, a good treatment result may be predicted when the concentration of TIMP-1 is less than 107 ng/ml and a genotype of the rs10033464 is GG, due to relatively low values of the HR, as shown in FIG. 4.

Based on the results of the examples, it may be found that the recurrence rate after the catheter ablation in the patients with paroxysmal AF shows a significant difference when two factors, that is, the "concentration of TIMP-1" and "genotypes of rs10033464" are combined and used, unlike the control group and the patients with persistent AF.

Thus, the method may be usefully applied to predict a risk of a recurrence after treatment of a patient determined to have paroxysmal AF.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of predicting a risk of recurrence of paroxysmal atrial fibrillation (AF) in a patient after treatment of AF, the method comprising following steps:
   (1) obtaining a blood sample from the patient;
   (2) measuring a concentration of tissue inhibitor of metalloproteinase (TIMP)-1 of 107 ng/ml or greater in the sample;
   (3) detecting the presence of a G/T or T/T genotype of the rs10033464 polymorphism in nucleic acid from the sample;
   (4) predicting a high risk of recurrence of paroxysmal AF in said patient based on said measured concentration of TIMP-1 of 107 ng/ml or greater and said G/T or T/T genotype at rs10033464; and
   (5) treating said patient with an additional treatment for AF, wherein said additional treatment is a pharmacological treatment for AF.

2. The method of claim 1, wherein the blood sample is selected from the group consisting of whole blood, a serum, and plasma.

3. The method of claim 1, wherein the detecting the genotype at rs10033464 is performed by at least one method selected from the group consisting of a hybridization by a microarray, an allele-specific polymerase chain reaction (PCR), a dynamic allele-specific hybridization (DASH), a PCR extension assay, a PCR-single-strand conformation polymorphism (SSCP) assay, and a PCR-restriction fragment length polymorphism (RFLP) assay.

4. The method of claim 1, wherein said pharmacological treatment is selected from the group consisting of propaphenone, flecainide, pilsicainide, amiodarone, sotalol or dronedarone, digoxin, beta blockers, verapamil, diltiazem, an anticoagulant agent, and an antiplatelet agent.

* * * * *